United States Patent [19]

Hammar et al.

[11] 4,143,152

[45] Mar. 6, 1979

[54] ANTI-MICROBIAL (2-NITRO-3-PHENYL BENZOFURANYL)-PHENYLALKANOIC ACIDS AND DERIVATIVES

[75] Inventors: Walton J. Hammar; Mark A. Rustad, both of St. Paul, Minn.

[73] Assignee: Riker Laboratories, Inc., Northridge, Calif.

[21] Appl. No.: 862,013

[22] Filed: Dec. 19, 1977

[51] Int. Cl.[2] .................... A61K 31/345; C07D 307/82

[52] U.S. Cl. ................................ 424/285; 260/346.22; 260/346.73

[58] Field of Search ....................... 260/346.22, 346.73; 424/285

[56] References Cited

U.S. PATENT DOCUMENTS

| | | | |
|---|---|---|---|
| 4,048,323 | 9/1977 | Scherrer | 260/346.22 |
| 4,066,782 | 1/1978 | Scherrer | 260/346.22 |
| 4,067,993 | 1/1978 | Scherrer | 260/346.22 |

FOREIGN PATENT DOCUMENTS 846502 3/1977 Belgium.

*Primary Examiner*—Henry R. Jiles
*Assistant Examiner*—Bernard Dentz
*Attorney, Agent, or Firm*—Cruzan Alexander; Donald M. Sell; Donald C. Gipple

[57] ABSTRACT

Compounds wherein a phenylalkanoic acid is substituted by a 2-nitro-3-phenylbenzofuran group which are active as antimicrobial agents, processes for their use and intermediates therefor are described.

14 Claims, No Drawings

ANTI-MICROBIAL (2-NITRO-3-PHENYL BENZOFURANYL)-PHENYLALKANOIC ACIDS AND DERIVATIVES

BACKGROUND OF THE INVENTION

This invention relates to a class of phenylalkanoic acid compounds which are substituted by a 2-nitro-3-phenylbenzofuran group and to ester, amide, acyl halide and pharmaceutically acceptable salts of said acids, to the use of these compounds as antimicrobial agents and to synthetic intermediates useful for their preparation.

Compounds wherein 2-nitro-3-phenylbenzofuran is substituted by an alkanoic acid group are known to have antimicrobial activity (see Belgian Pat. No. 846,502 and German Offenlegungsschrift No. P 2642877). However, in such compounds the alkanoic acid group is substituted on the 3-phenylbenzofuran portion of the molecule. Furthermore, they are prepared by different synthetic sequences and from different types of starting materials than are the compounds of the present invention.

DETAILED DESCRIPTION OF THE INVENTION

The present invention relates to optionally substituted phenylalkanoic acids substituted by a 2-nitro-3-phenylbenzofuran group and bonded to the benzo ring of the benzofuran by a sigma bond and to esters, amides, acyl halides and pharmaceutically acceptable salts of the acids. It also relates to the use of the compounds as antimicrobial agents and to synthetic intermediates useful for the preparation of the compounds of the invention.

According to the present invention, there is provided a class of compounds of the formula

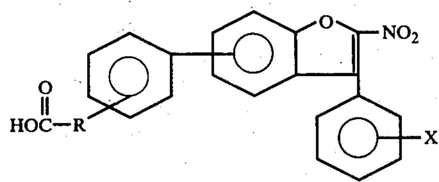

wherein R is straight or branched chain alkylene of one to four carbon atoms and X is hydrogen, halogen, alkyl or alkoxy of one to three carbon atoms, or an ester, acyl halide or pharmaceutically acceptable salt thereof.

The free acids are ordinarily white or yellowish to brown crystalline or amorphous materials when purified. They are substantially insoluble in water or aliphatic hydrocarbons and are more soluble in lower alcohols, halogenated solvents, benzene, dimethylformamide and the like. The esters and amides are generally somewhat more soluble in organic solvents. The alkali metal salts have appreciable solubility in water and lower alcohols.

All of the compounds of the invention are active against bacteria, and some are also active against other microorganisms, including fungi and protozoa, in vitro and topically. Thus, they can be used for disinfecting and sterilizing, for example of medical and dental equipment, as components of disinfecting solutions. The compounds are particularly useful as antibacterial agents. In general, the compounds are also active in vivo in animal tests. The free acids are presently preferred for many purposes due to their generally higher levels of antimicrobial activity in vitro. For applications in which water solubility is of importance, the salts are ordinarily used.

The compounds of the invention in which R is methylene ($-CH_2-$) form a presently preferred subclass due to their high in vitro activity. Other presently preferred subclasses are the compounds in which the five (5) position of the benzofuran moiety is substituted by the phenylacetic acid group (due to their high degree of antimicrobial activity) and in which the benzofuran ring is bonded para to the alkanoic acid group. The particularly preferred compounds (which have broad spectra of antibacterial activity and activity versus *Pseudomonas aeruginois*) are 2-nitro-3-phenyl-5-[(4-carboxymethyl)phenyl]benzofuran and 2-nitro-3-(3-chlorophenyl)-5-[(4-carboxymethyl)phenyl]benzofuran.

Alkali metal, alkaline earth, aluminum, iron and other metal and amine salts are often the equivalents of the corresponding acid-form compounds and offer advantages in solubility, absorption, persistence, formulation and the like. The salts are of interest for topical uses (e.g. ophthalmic and dermatologic). Alkali metal salts (e.g. Na and K) are preferred. The esters and amides are also useful for modifying the solubility, persistence, absorption and other properties.

Among the other important subclasses of the compounds of the invention which are represented by specific examples herein are those in which R is methylene or methylmethylene, in which S is methyl and lower alkyl esters, acyl chlorides, amides and alkyl amides.

In compounds of the invention wherein R is branched, optically active compounds are obtained which are included within the scope of the invention.

The free acids of the invention are prepared by several methods (sometimes requiring multiple-step reactions) including:

A. the direct nitration of phenylalkanoic acids substituted on the benzo ring by a 3-phenylbenzofuran group;

B. preparing an intermediate phenylalkanoic acid substituted on the benzo ring by a 2-halo-3-phenylbenzofuran group (by the specific halogenation of the 2 position of the 3-phenylbenzofuran group of the respective 2-unsubstituted compound) followed by replacement of the halogen substituent with a nitro group employing a nitrating reagent;

C. the acid hydrolysis of the corresponding phenylalkanoic acid ester or amide substituted on the benzo ring by a nitrophenylbenzofuran group.

The direct process (process A) can be carried out with fuming nitric acid in acetic acid or acetic anhydride or with dinitrogen tetroxide in an inert solvent such as dichloromethane. In order to avoid aromatic nitration moderate temperatures of 0° to 30° C. are generally used.

The halogenation step of process B may be bromination or iodination. The bromination can be carried out using N-bromosuccinimide or preferably bromine in a suitable solvent such as dichloromethane or acetic acid. Bromination is carried out under mild conditions, e.g. 0° to 30° C. to avoid aromatic bromination. The bromo compound may be isolated or used without isolation. Isolation may be carried out by extraction, precipitation by the addition of a non-solvent such as water, evaporation of volatile reaction components, etc. The iodination is carried out e.g. with molecular iodine in the presence of yellow mercuric oxide in an inert solvent such as benzene. Generally these reactions are carried out at about 25° to 125° C., for example at the reflux temperature of the solvent.

In the final step of process B, the 2-halo substituent can be displaced by means of selecting nitrating agents, such as strong nitric acid solution, for example 70 percent aqueous nitric acid, dinitrogen tetroxide in e.g. acetic acid or dichloromethane solution or a mixture of sodium nitrite and a strong acid. When 70 percent nitric acid is used as the nitrating reagent for 2-halo derivatives, preferably about two or three moles each of sodium nitrite and nitric acid per mole of benzofuran is included. About four to twenty milliliters of acetic acid per gram of 2-halobenzofuran derivative is used, depending on its solubility. It is desired to maintain the dissolution of the 2-halobenzofuran derivative, and the amount of acetic acid and the reaction temperature is adjusted to achieve this result readily. The reaction temperature is about 25° to 100° C., and preferably about 60° to 80° C. when the halogen is bromine.

It has been found that a mixture of sodium nitrite, sulfuric acid and acetic acid will also nitrate the 2-halobenzofuran derivatives successfully in the 2-position. The 2-halobenzofuran derivative is dissolved in acetic acid to maintain solution (up to 20 ml. per gram required), and concentrated sulfuric acid is added, from two to ten milliliters per gram of benzofuran. Sodium nitrite is then added to the solution. The reaction temperature is about 20° to 100° C., and preferably about 55° C. The sodium nitrite can be replaced in this reaction by other metal nitrites such as potassium nitrite. In each of the preceding nitration methods, polynitration is a side-reaction.

A combination of dinitrogen tetraoxide in an inert solvent in the presence of an alkene is one presently preferred nitration method according to process B, with acetic acid and dichloromethane as the preferred solvents. For example, two to five liters of acetic acid per mole of benzofuran or halobenzofuran derivatives are generally used. At least one mole of nitrogen tetroxide per mole of benzofuran is used. The exact amount depends on the rate of reaction desired, the extent of volatilization and other physical losses and the amount of competitive addition to the added olefin. An alkene is preferably used with a 2-bromobenzofuran intermediate to remove the elements of $BrNO_2$ and minimize bromination as a side reaction. Cyclohexene is satisfactory for this use. Preferably equimolar amounts of alkene and nitrogen tetroxide are used. The olefin is chosen to be less reactive to $N_2O_4$ than the benzofuran but more reactive to $BrNO_2$ than the benzofuran. An acidic olefin, e.g. 3-cyclohexene carboxylic acid, is advantageous when the nitrated product is neutral. The temperature of these reactions is generally about 0° to 80° C., preferably 20° to 45° C. for bromine exchange and about 0° to 25° C. for iodine exchange and direct nitration. When 2-iodobenzofurans are used, the olefin is not required (since the iodine is generally unreactive to the benzofuran under the reaction conditions) and only one-half mole of $N_2O_4$ is theoretically then required.

The phenylalkanoic acid esters and amides substituted by a 2-nitro-3-phenylbenzofuran group for use in process C can be prepared by nitration of phenylalkanoic acid esters and amides substituted by a 2-unsubstituted or 2-halo-3-phenylbenzofuran group. These esters, preferably lower alkyl esters, and amides are readily hydrolyzed by conventional acid hydrolysis. Amides are preferably prepared from acyl halides as described hereinafter.

The pharmaceutically acceptable salts of the invention are readily prepared by reaction of the corresponding free acids with the appropriate base and optionally in a suitable solvent and evaporation to dryness. The base used to prepare the salts may be organic, e.g. sodium methoxide or an amine, or inorganic. Furthermore, other salts which are not pharmaceutically acceptable may be useful for the synthesis of the acid compounds or other, acceptable salts or other useful intermediates such as esters. The acyl halides of the invention are prepared by reaction of the free acid with thionyl chloride, generally in a non-reactive solvent such as dichloromethane or benzene. The esters of the invention are prepared as described above in connection with their use in process C. The amides are generally prepared by reaction of the acyl halides with the desired amine. The free acids can also be prepared from the corresponding esters, amides and acyl halides by methods known to those skilled in the art.

The novel classes of intermediates provided by this invention include compounds of the formula

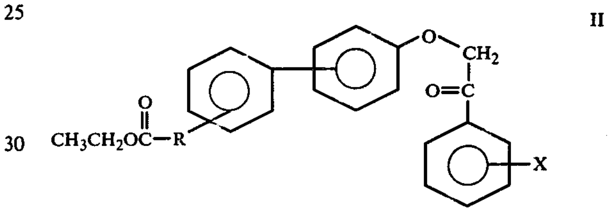

wherein R and X are as defined hereinabove. These compounds are prepared from the X-substituted α-bromoacetophenones which are generally known or easily prepared by known methods and from (hydroxyphenyl)-phenylacetic acids, which are also known compounds, or prepared by known methods from available starting materials. Preparation is by reaction, generally at reflux (about 30° to 120° C.) in an inert solvent such as benzene, acetone and the like, in the presence of a weak base such as sodium or potassium carbonate. Increased basicity may be used to increase the rate of reaction.

Another class of novel intermediates is compounds of the formula

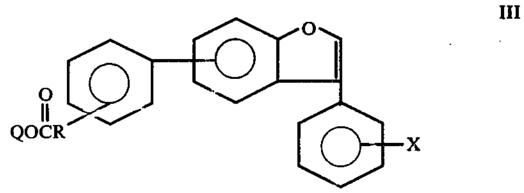

wherein R and X are as defined hereinabove and Q is hydrogen or ethyl. These compounds are prepared by cyclization or by heating at 40° to 120° C. in polyphosphoric acid of compounds of formula II to give compounds wherein Q is ethyl, followed by hydrolysis to give compounds wherein Q is hydrogen.

Another novel class of intermediates are compounds wherein the 2 position is substituted by bromine. These are prepared by bromination of the compounds of formula III with bromine in an inert solvent such as acetic acid or dichloromethane under mild conditions, e.g. 0° to 30° C., to avoid bromination of the benzo and/or phenyl ring.

The antimicrobial activity of the compounds is evaluated using a variation of the original agar plate diffusion method of Vincent and Vincent (e.g. see Vincent, J. G., and Vincent, Helen W., Proc. Soc. Exptl. Biol. Med. 55:162–164, 1944, and Davis, B. D., and Mingioli, E. S., J. Bac. 66:129–136, 1953). Using this test, the compounds of the invention have been found to have a broad spectrum of activity against both gram-positive and gram-negative microorganisms. The procedure provides information on the amount of a compound required to give complete inhibition, partial inhibition or no inhibition of microbial growth on agar plates. The microbial growth on each plate is read visually, and minimal inhibitory concentrations are recorded.

The microorganisms used are: *Staphylococcus aureus, Bacillus subtilus, Pseudomonas aeruginosa, Escherichi coli, Streptococcus sp.* (strains isolated from dental caries in rats or hamsters at the National Institute of Dental Health and grown in PFY or APT agar), *Asperigillus niger, Candida albicans, Mima polymorpha, Herellea vaginicola, Klebsiella pneumoniae* and *Streptococcus fecaelis.*

These are selected representatives of various bacterial and fungal classes and broad spectrum activity can be predicted as a result of activity against them. All of the compounds of the invention possess antimicrobial activity towards one or more of the above microorganisms. The compounds maintain high activity against the microorganisms either in the absence or presence or 10 percent horse serum.

The acute oral toxicity of the compounds of the invention generally is moderate to low compared with the effective oral dose, and they have a good to excellent therapeutic ratio.

The compounds of the invention may be formulated by incorporating them into conventional pharmaceutical carrier materials, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing the object to be treated therein, or by local application to an infected area. The amount of compound to be used for treatment of a microbial infection will be an effective amount less than a toxic amount. The amount to be administered to a subject and route of administration to control an infection will depend on the species of organism, the sex, weight, physical condition of the subject, the locus of the infection and many other factors, but this judgment is well within the skill of the art. Usually the amount will be less than 100 mg/kg per dose. Conveniently the oral treatment is administered in the form of the usual pharmaceutical preparation such as capsules, tablets, emulsions, solutions, suppositories and the like. Excipients, fillers, coatings, etc. are employed with tablets or capsules, as is well known in the art.

It is often advantageous to combine the compounds of this invention with other antimicrobial compounds such as coccidiostats, anthelmintics, antifungals, antibiotics, steroids, or antibacterial agents, or to combine more than one compound described herein in a single composition.

Certain of the compounds are also active antiparasitics as shown by activity in laboratory tests versus the protozoa *Trichomonas sp.* and *T. vaginalis.* In view of the outstanding antimicrobial activity of the compounds, they would also be expected to be effective growth promoters in various animal and bird species.

The following examples are given for the purpose of further illustrating the procedures of the present invention, but are not intended, in any way, to be limiting on the scope thereof. Thus, while the majority of the examples relate to the free acid compounds, the other compounds of the invention can also be prepared. The melting points are uncorrected, the temperatures are in degrees Centigrade and the pressures in millimeters of mercury.

EXAMPLE 1

Step A. A mixture of 10 g. (0.039 mole) of ethyl 4-(4-hydroxyphenyl)phenylacetate, 7.8 g. (0.039 mole) of α-bromoacetophenone and 11 g. (0.8 mole) of potassium carbonate in 250 ml. of benzene is heated at its reflux temperature for about six days. The mixture is washed with water, twice with 100 ml. of 10 percent sodium hydroxide, then 100 ml. of 6N hydrochloric acid and dried over calcium sulfate. The solvent is evaporated to provide a residue which is triturated with hexane. Recrystallization of the solid product from an ethyl acetate-hexane mixture provides α-4-[4-(carboethoxyethyl)phenoxy]acetophenone. Structural assignment is confirmed by infrared and nuclear magnetic resonance spectral analysis.

Step B. A mixture of 5.9 g. of acetophenone product from step A and 60 g. of polyphosphoric acid is heated at 70° to 80° C. for 1.5 hours. Thin layer chromatographic analysis indicates reaction is complete. The mixture is poured in 600 ml. of water and stirred, then extracted with chloroform. The extracts are dried over magnesium sulfate, then evaporated to provide 3-phenyl-5-[(4-carboethoxymethyl)phenyl]benzofuran. Structural assignment is confirmed by infrared and nuclear magnetic resonance spectral analysis.

Step C. A mixture of the benzofuran product from step B, 50 ml. of 10 percent sodium hydroxide solution and 100 ml. of ethanol is heated on a steam bath for two hours. The ethanol is evaporated and the residual solution is acidified with 6N hydrochloric acid. The product gradually crystallizes and is recrystallized from aqueous ethanol to give 3-phenyl-5-[(4-carboxymethyl)-phenyl]benzofuran. Structural assignment is confirmed by infrared and nuclear magnetic resonance spectral analysis.

Step D. A solution of 3.1 g. of 3-phenyl-5-[(4-carboxymethyl)phenyl]benzofuran and 2 g. of dinitrogen tetraoxide in 200 ml. of dichloromethane is stirred for about 16 hours at about 20° C. The solvent is evaporated, and the residue is eluted from silica gel with chloroform. The product is obtained as a yellow solid and recrystallized from a benzene-hexane mixture to provide 2-nitro-3-phenyl-5-[(4-carboxymethyl)phenyl)-benzofuran, m.p. 194°–197° C.

| Analysis: | %C | %H | %N |
|---|---|---|---|
| Calculated for $C_{22}H_{15}NO_5$: | 70.8; | 4.0; | 3.7 |
| Found: | 70.1; | 3.9; | 3.8. |

EXAMPLE 2

A chloroform solution of 3-phenyl-5-[(4-carboethoxymethyl)phenyl]benzofuran (preparation shown in step B of Example 1) is brominated to provide 2-bromo-3-phenyl-5-[(4-carboethoxymethyl)phenyl]benzofuran. A solution of 1.32 g. of this bromobenzofuran is dissolved in 100 ml. of hot acetic acid and 0.51 g. of cyclohexene. To this solution is added 0.57 g. of dinitrogen tetraoxide in 5 ml. of acetic acid. The solution is stirred at 20° C. for 40 hours, then evaporated to provide a residue. The residue is mixed with 10 ml. of hexane and 10 ml. of isopropanol, concentrated to 10 ml. and allowed to crystallize. The product is 2-nigtro-3-phenyl-5-[(4-carboethoxymethyl)phenyl]benzofuran, m.p. 79°-80° C.

| Analysis: | %C | %H | %N |
|---|---|---|---|
| Calculated for $C_{24}H_{19}NO_5$: | 71.9; | 4.8; | 3.5 |
| Found: | 71.4; | 4.7; | 3.5. |

Using the method of Example 1 and starting with the known intermediates shown, the following compounds of the invention are prepared.

TABLE I

| Ex. No. | Starting Materials | | Product |
|---|---|---|---|
| 3 | HOCH$_2$C(=O)- biphenyl -OH | Br-CH$_2$-C(=O)- phenyl -CH$_3$ | HOCCH$_2$(=O) ... NO$_2$ ... CH$_3$ |
| 4 | HOCH$_2$C(=O) ... OH | Br-CH$_2$-C(=O)- phenyl | HOCCH$_2$(=O) ... NO$_2$ |
| 5 | HOCHC (O, CH$_3$) ... OH | Br-CH$_2$-C(=O)- phenyl -CH$_3$ | HOCHC (O, CH$_3$) ... NO$_2$ ... CH$_3$ |
| 6 | HOCH$_2$C(=O) ... OH | Br-CH$_2$-C(=O)- phenyl | HOCCH$_2$(=O) ... NO$_2$ |
| 7 | HOC(=O)-CH$_2$ ... OH | Br-CH$_2$-C(=O)- phenyl | HOC(=O)-CH$_2$ ... NO$_2$ |

EXAMPLE 8

Step A. A mixture of 18 g. (0.048 mole) of 2-nitro-3-phenyl-5-[(4-carboxymethyl)phenyl]benzofuran (preparation shown in Example 1) and 600 ml. of thionyl chloride is heated at its reflux temperature for four hours, cooled and evaporated in vacuo. The residue is diluted with dichloromethane and re-evaporated thrice to provide the desired acid chloride according to infrared spectral analysis.

Step B. Using 3.14 g. of the acid chloride prepared in step A in 100 ml. of dichloromethane, the solution is cooled with an ice bath, and ammonia gas is bubbled in until the solution is basic. After stirring cold for one hour the solution is mixed and washed thoroughly with 20 ml. of 10 percent sodium hydroxide solution. The dichloromethane fraction is then washed twice with 20 ml. of water. The organic layer is evaporated in vacuo to provide a solid residue which is washed with hexane to provide a yellow powder which is eluted through a silica gel column with dichloromethane to provide 2-nitro-3-phenyl-5-[(4-carboxamidomethyl)phenyl]benzofuran, m.p. 210°-211° C.

| Analysis: | %C | %H | %N |
|---|---|---|---|
| Calculated for $C_{22}H_{16}N_2O_4$: | 70.9; | 4.3; | 7.5 |
| Found: | 70.2; | 4.3; | 6.9. |

EXAMPLE 9

Using 3.14 g. of the acid chloride of Example 8 in 100 ml. of dichloromethane, methylamine gas is bubbled into the cold solution until the solution reaches pH 8. After stirring for about one hour, the solution is washed with 20 ml. of 10 percent sodium hydroxide solution, then twice with water. The organic layer is evaporated to dryness, and the solid residue is washed with hexane, then eluted through a silica gel column with dichloromethane to provide three fractions, the second of which is determined to be 2-nitro-3-phenyl-5-[(4-N-methylcarboxamidomethyl)phenyl]benzofuran, m.p. 190°-191° C. by infrared and nuclear magnetic resonance spectral analysis.

| Analysis: | %C | %H | %N |
|---|---|---|---|
| Calculated for $C_{23}H_{18}N_2O_4$: | 71.5; | 4.7; | 7.2 |
| Found: | 71.0; | 4.7; | 6.4. |

EXAMPLE 10

3-(4-Chlorophenyl)-5-[(4-carboxymethyl)phenyl]-benzofuran is prepared using the method of Example 1, steps A, B and C. From this intermediate is prepared 3-(4-chlorophenyl)-5-[(4-carboxymethyl)phenyl]-2-nitrobenzofuran using the method of Example 2. The initial product (m.p. 181°-182° C.) is relatively impure but is shown by thin layer chromatography to be the desired product contaminated by some of the 2-bromo intermediates.

What is claimed is:

1. A compound of the formula

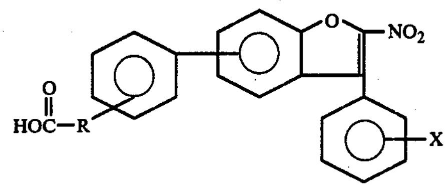

wherein R is straight or branched chain alkylene of one to four carbon atoms and X is hydrogen, halogen or alkyl or alkoxy of one to three carbon atoms, or a lower alkyl ester, an N-unsubstituted or alkyl amide or an acyl halide or pharmaceutically acceptable salt thereof.

2. A compound according to claim 1 wherein R is methylene.

3. A compound according to claim 1 in which the five position of the benzofuran ring is substituted by a phenylacetic acid group.

4. The compound 2-nitro-3-phenyl-5-[(4-carboxymethyl)phenyl]benzofuran according to claim 3.

5. The compound 2-nitro-3-(3-chlorophenyl)-5-[(4-carboxymethyl)phenyl]benzofuran according to claim 3.

6. The compound 2-nitro-3-phenyl-5-[(4-carboxamidomethyl)phenyl]benzofuran according to claim 1.

7. The compound 2-nitro-3-phenyl-5-[(4-N-methylcarboxamidomethyl)phenyl]benzofuran according to claim 1.

8. The compound 2-nitro-3-phenyl-5-[(4-carboethoxymethyl)phenyl]benzofuran according to claim 1.

9. A method for arresting or inhibiting the growth of microorganisms comprising contacting microorganisms with a compound according to claim 1 in an amount sufficient to arrest or inhibit the growth of said microorganisms.

10. A method according to claim 9 for arresting or inhibiting the growth of bacteria.

11. A compound of the formula

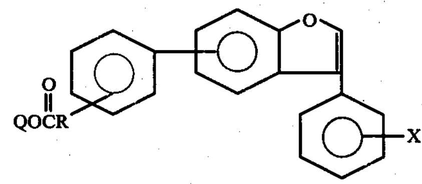

wherein R is straight or branched chain alkylene of one to four carbon atoms and X is hydrogen, halogen or alkyl or alkoxy of one to three carbon atoms and Q is hydrogen or ethyl.

12. A compound according to claim 11 in which the R is bonded to the four position of the ring.

13. A compound of the formula

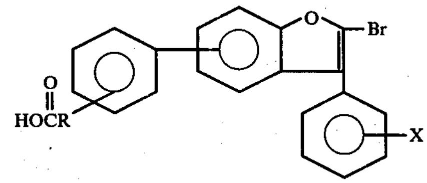

wherein R is straight or branched chain alkylene of one to four carbon atoms and X is hydrogen, halogen or alkyl or alkoxy of one to three carbon atoms.

14. A compound according to claim 13 in which the R is bonded to the four position of the ring.

* * * * *